(12) United States Patent
Kirkpatrick et al.

(10) Patent No.: US 8,530,859 B2
(45) Date of Patent: Sep. 10, 2013

(54) METHOD AND SYSTEM FOR STERILIZING OBJECTS BY THE APPLICATION OF GAS-CLUSTER ION-BEAM TECHNOLOGY

(75) Inventors: Sean R. Kirkpatrick, Littleton, MA (US); Richard C. Svrluga, Newton, MA (US)

(73) Assignee: Exogenesis Corporation, Billerica, MA (US)

( * ) Notice: Subject to any disclaimer, the term of this patent is extended or adjusted under 35 U.S.C. 154(b) by 550 days.

(21) Appl. No.: 12/492,661

(22) Filed: Jun. 26, 2009

(65) Prior Publication Data

US 2009/0321658 A1  Dec. 31, 2009

Related U.S. Application Data

(60) Provisional application No. 61/075,957, filed on Jun. 26, 2008.

(51) Int. Cl.
*G21K 5/04* (2006.01)
*A61L 2/00* (2006.01)

(52) U.S. Cl.
USPC .............. 250/455.11; 250/453.11; 250/492.1; 250/492.3; 422/1; 422/20; 422/22; 422/23

(58) Field of Classification Search
USPC ......... 422/1, 20, 22, 23; 250/453.11, 455.11, 250/492.1, 492.3, 493.1
See application file for complete search history.

(56) References Cited

U.S. PATENT DOCUMENTS

| 4,935,623 | A | 6/1990 | Knauer |
| 5,459,326 | A | 10/1995 | Yamada |
| 5,814,194 | A | 9/1998 | Deguchi et al. |
| 6,033,484 | A | 3/2000 | Mahoney |
| 6,486,478 | B1 | 11/2002 | Libby et al. |
| 6,491,800 | B2 | 12/2002 | Kirkpatrick et al. |
| 6,676,989 | B2 | 1/2004 | Kirkpatrick et al. |
| 2003/0198570 | A1* | 10/2003 | Asahara et al. ................. 422/22 |
| 2007/0131539 | A1* | 6/2007 | Torimoto ..................... 204/240 |
| 2008/0010947 | A1 | 1/2008 | Huang et al. |
| 2008/0169416 | A1 | 7/2008 | Thompson et al. |
| 2009/0084977 | A1* | 4/2009 | Mack et al. ............... 250/423 R |
| 2009/0140165 | A1 | 6/2009 | Hautala et al. |
| 2009/0321658 | A1 | 12/2009 | Kirkpatrick et al. |
| 2010/0154360 | A1* | 6/2010 | Py .................................. 53/452 |

FOREIGN PATENT DOCUMENTS

| JP | H10-66721 A | 3/1998 |
| WO | 2006089134 A2 | 8/2006 |

OTHER PUBLICATIONS

International Preliminary Report on Patentability issued on Jan. 5, 2011 for PCT/US09/48846. Applicant: Exogenesis Corporation.
International Search Reported dated Jan. 18, 2010 for PCT/US09/48846. Applicant: Exogenesis Corporation.
Written Opinion dated Jan. 18, 2010 for PCT/US09/48846. Applicant: Exogenesis Corporation.

(Continued)

*Primary Examiner* — Robert Kim
*Assistant Examiner* — Nicole Ippolito
(74) *Attorney, Agent, or Firm* — Burns & Levinson LLP; Jerry Cohen; David W Gomes

(57) ABSTRACT

Methods and systems for sterilization of objects by gas-cluster ion-beam (GCIB) irradiation are disclosed. The sterilization may be in conjunction with other beneficial GCIB surface processing of the objects. The objects may be medical devices or surgically implantable medical prostheses.

8 Claims, 5 Drawing Sheets

(56) References Cited

OTHER PUBLICATIONS

Yamada, I. et al., Nano-scale surface modification using gas cluster ion beams—A development history and review of the Japanese nanotechnology program, Surface and Coatings Technology, vol. 201, Issues 19-20, Aug. 5, 2007, pp. 8579-8587.

International Search Reported dated May 29, 2012 for PCT/US12/22567. Applicant: Exogenesis Corporation.

Written Opinion dated May 29, 2012 for PCT/US12/22567. Applicant: Exogenesis Corporation.

* cited by examiner

METHOD AND SYSTEM FOR STERILIZING OBJECTS BY THE APPLICATION OF GAS-CLUSTER ION-BEAM TECHNOLOGY

CROSS REFERENCE TO RELATED APPLICATIONS

The present application claims priority from U.S. Provisional Patent Application No. 61/075,957, filed Jun. 26, 2008, entitled METHOD AND SYSTEM FOR STERILIZING OBJECTS BY THE APPLICATION OF GAS CLUSTER ION BEAM TECHNOLOGY, the contents of which are hereby incorporated by reference herein.

FIELD OF THE INVENTION

This invention relates generally to the sterilization of objects including medical devices by irradiation by gas-cluster ion-beam (GCIB). The sterilization may be performed in combination with other GCIB processing of the object.

BACKGROUND OF THE INVENTION

Sterilization of objects such as medical devices or surgically implantable devices or prostheses has traditionally been done by a variety of methods including steam or dry heating, ultraviolet, x-ray, or gamma-ray irradiation, plasma sterilization, conventional ion beam irradiatiation, and exposure to sterilant gases or germicidal fluids.

Gas-cluster ions are formed from large numbers of weakly bound atoms or molecules sharing common electrical charges and they can be accelerated to have high total energies. Gas-cluster ions disintegrate upon impact and the total energy of the cluster ion is shared among the constituent atoms. Because of this energy sharing, the atoms are individually much less energetic than in the case of un-clustered conventional ions and, as a result, the atoms only penetrate to much shallower depths than would conventional ions. Surface effects can be orders of magnitude stronger than corresponding effects produced by conventional ions, thereby making important micro-scale surface modification effects possible that are not possible in any other way.

The concept of gas-cluster ion-beam (GCIB) processing has only emerged in recent decades. Using a GCIB for dry etching, cleaning, and smoothing of materials, as well as for film formation is known in the art and has been described, for example, by Deguchi, et al. in U.S. Pat. No. 5,814,194, "Substrate Surface Treatment Method", 1998. Because ionized gas-clusters containing on the order of thousands of gas atoms or molecules may be formed and accelerated to modest energies on the order of a few thousands of electron volts, individual atoms or molecules in the clusters may each only have an average energy on the order of a few electron volts. It is known from the teachings of Yamada in, for example, U.S. Pat. No. 5,459,326, that such individual atoms are not energetic enough to significantly penetrate a surface to cause the residual sub-surface damage typically associated with plasma polishing or conventional monomer ion beam processing. Nevertheless, the clusters themselves are sufficiently energetic (some thousands of electron volts) to effectively etch, smooth, or clean hard surfaces, or to perform other shallow surface modifications.

Because the energies of individual atoms within a gas-cluster ion are very small, typically a few eV, the atoms penetrate through only a few atomic layers, at most, of a target surface during impact. This shallow penetration of the impacting atoms means all of the energy carried by an entire cluster ion is consequently dissipated in an extremely small volume in the top surface layer during an extremely short time interval. This is different from the case of ion implantation, which is normally done with conventional ions and where the intent is to penetrate into the material, sometimes penetrating several thousand angstroms, to produce changes in both the surface and sub-surface properties of the material. Because of the high total energy of the cluster ion and extremely small interaction volume of each cluster, the deposited energy density at the impact site is far greater than in the case of bombardment by conventional ions and the extreme conditions permit material modifications not otherwise achievable.

Irradiation by GCIB has been successfully applied in a variety of surface modification processes including cleaning, smoothing, surface infusion, deposition, etching, and changing surface characteristics such as making a surface more or less wettable. The cleaning, smoothing, etching, and wettability modification processes (for example) are sometimes useful for improving the surfaces of medical devices, surgical implants, and medical prostheses. It is desirable and necessary that many types of medical devices, implants, and prostheses be sterile for use in their intended applications.

It is therefore an object of this invention to provide methods and apparatus for surface sterilization of objects including medical devices, surgical implants, and/or medical prostheses by GCIB irradiation.

It is another object of this invention to provide methods and apparatus for multi-step processing of objects including a step of surface sterilization by GCIB irradiation in combination with another GCIB surface processing step on the same object.

It is a further object of this invention to provide methods and apparatus for surface sterilization of objects, without significantly elevating the temperature of the bulk of the object and without the use of toxic materials.

SUMMARY OF THE INVENTION

The objects set forth above, as well as further and other objects and advantages of the present invention, are achieved as described hereinbelow.

One embodiment of the present invention provides method for sterilizing a workpiece, comprising the steps of: providing a reduced pressure chamber; forming an accelerated gas-cluster ion-beam having a path in the reduced pressure chamber; providing a workpiece holder in the reduced pressure chamber for holding the workpiece in the accelerated gas-cluster ion-beam path; and irradiating at least a portion of a surface of the workpiece with the accelerated gas-cluster ion-beam for sterilizing the portion.

The irradiating step may introduce a dose of at least $10^{13}$ ions/cm$^2$ to the at least a portion of the surface of the workpiece. The forming step may include accelerating the gas-cluster ion-beam using an acceleration potential of at least 2 kV. The forming step may comprise forming a gas-cluster ion-beam comprising a noble gas or a mixture of a noble gas with oxygen. The at least a portion of a surface may be an entire surface. The step of providing a workpiece holder may further comprise sterilizing the workpiece holder.

Another embodiment of the present invention provides a method for sterilizing a workpiece, comprising the steps of: a. providing a chamber having an interior and a workpiece holder in the interior; b. initially sterilizing the workpiece holder and the interior of the chamber; c. forming an accelerated gas-cluster ion-beam; d. loading a workpiece onto the workpiece holder to be held thereby for sterilization; e. reducing the pressure in the chamber; f. directing the accelerated gas-cluster ion-beam onto the workpiece; g. irradiating at least a portion of a surface of the workpiece with the accelerated gas-cluster ion-beam; h. discontinuing irradiation when the at least a portion of a surface of the workpiece has received a predetermined dose; and i. unloading the workpiece from the workpiece holder and removing it from the chamber.

The method may further comprise the step of venting the chamber with a sterile gas. The method may further comprise the step of: repeating steps d. through i. at least once. The at least a portion of a surface may be an entire surface. The step of unloading may include placing the workpiece directly into a sterile container.

Yet another embodiment of the present invention provides a method for sterilizing a workpiece, comprising the steps of: providing a chamber having an interior and a workpiece holder; initially sterilizing the workpiece holder and the interior of the chamber; loading a workpiece onto the workpiece holder to be held thereby; forming a first accelerated gas-cluster ion-beam; directing the first accelerated gas-cluster ion-beam onto the workpiece; first processing the workpiece by irradiating at least a first portion of the surface of the workpiece with the first accelerated gas-cluster ion-beam; discontinuing first processing when the at least a first portion of the surface of the workpiece has received a predetermined dose; forming a second accelerated gas-cluster ion-beam; directing the second accelerated gas-cluster ion-beam onto the workpiece; second processing the workpiece by irradiating at least a second portion of the surface of the workpiece with the second accelerated gas-cluster ion-beam; discontinuing second processing when the at least a second portion of the surface of the workpiece has received a predetermined dose; unloading the workpiece from the workpiece holder and removing it from the chamber; and wherein either of the first processing step or the second processing step is a sterilizing step. The at least a first portion of the surface and the at least a second portion of the surface may be the same portion of the surface.

Still another embodiment of the present invention provides apparatus for sterilizing a workpiece, comprising: a reduced pressure chamber having an interior; a sterilizer adapted for initially sterilizing the interior of the reduced pressure chamber; an apparatus adapted for forming an accelerated gas-cluster ion-beam having a path in the interior of the reduced pressure chamber; a workpiece holder adapted for holding a workpiece in the path of the accelerated gas-cluster ion-beam in the interior of the reduced pressure chamber for receiving an irradiated gas-cluster ion-beam dose on at least a portion of the surface of the workpiece; a vent adapted for venting the reduced pressure chamber with a sterile gas; and a mechanism adapted for loading and/or unloading the workpiece onto or off of the holding means in the reduced pressure chamber and adapted for introducing and/or removing the workpiece from the reduced pressure chamber.

The workpiece holder may further comprise means for rotating, articulating, repositioning, or moving the workpiece to provide for receiving an irradiated gas-cluster ion-beam dose on multiple portions of the surface of the workpiece. The multiple portions of the surface the workpiece may comprise the entire surface of the workpiece.

The apparatus adapted for forming an accelerated gas-cluster ion-beam may further comprise: a nozzle; a skimmer; an ionizer; and an accelerator. The apparatus may further comprising a device adapted for scanning the accelerated gas-cluster ion-beam.

The sterilizer adapted for initially sterilizing the interior of the reduced pressure chamber may comprise means for introducing and removing a sterilant gas to/from the interior of the reduced pressure chamber. The sterilizer adapted for initially sterilizing the interior of the reduced pressure chamber may comprise means for irradiating the interior of the reduced pressure chamber with ultraviolet radiation.

For a better understanding of the present invention, together with other and further objects thereof, reference is made to the accompanying drawings and detailed description and in the appended claims.

DETAILED DESCRIPTION OF THE PREFERRED METHODS AND EMBODIMENTS

In the following description, for simplification of the drawings, item numbers from earlier figures may appear in subsequent figures without discussion. In such cases items with like numbers are like items and have the previously described features and functions.

Figure 1:
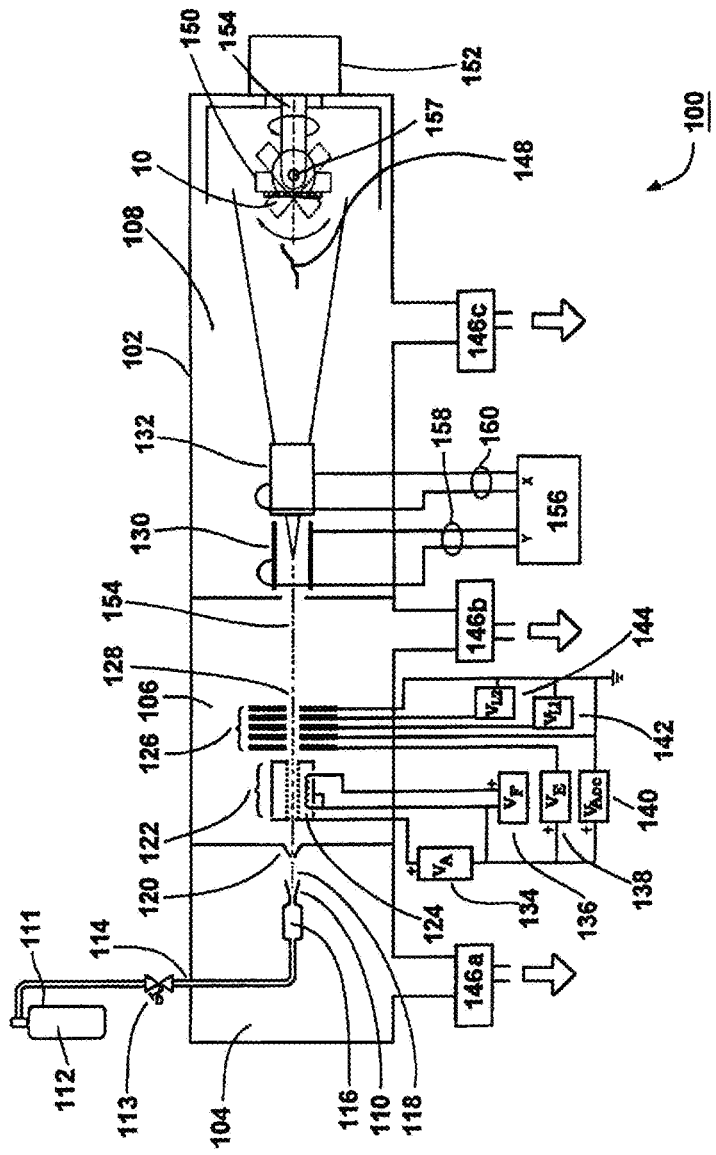
FIG. 1 is a is a schematic view of a GCIB processing system of the present invention.

FIG. 1 shows an embodiment of the (GCIB) processor 100 of this invention utilized for the surface sterilization of a workpiece 10 (which may be a medical device, surgical implant, or medical prosthesis or some other sterilizable object). Although not limited to the specific components described herein, the GCIB processor 100 is made up of a vacuum vessel 102 which is divided into three communicating chambers, a source chamber 104, an ionization/acceleration chamber 106, and a process chamber 108 which includes therein a uniquely designed workpiece holder 150 capable of positioning the medical device for uniform processing by a gas-cluster ion-beam.

During the processing method of this invention, the three chambers are evacuated to suitable operating pressures by vacuum pumping systems 146a, 146b, and 146c, respectively. A condensable source gas 112 (for example argon, $O_2$, etc.) stored in a cylinder 111 is admitted under pressure through gas metering valve 113 and gas feed tube 114 into stagnation chamber 116 and is ejected into the substantially lower pressure vacuum through a properly shaped nozzle 110, resulting in a supersonic gas jet 118. Cooling, which results from the expansion of the jet, causes a portion of the gas jet 118 to condense into clusters, each consisting of from several to several thousand weakly bound atoms or molecules, and typically having a distribution having a most likely size of hundreds to thousands of atoms or molecules. A gas skimmer aperture 120 partially separates the gas molecules that have not condensed into a cluster jet from the cluster jet so as to minimize pressure in the downstream regions where such higher pressures would be detrimental (e.g., ionizer 122, high voltage electrodes 126, and process chamber 108). Suitable condensable source gases 112 include, but are not necessarily limited to argon or other noble gases, oxygen, oxygen-containing gases, other reactive gases, and mixtures of these or other gases.

After the supersonic gas jet 118 containing gas clusters has been formed, the clusters are ionized in an ionizer 122. The ionizer 122 is typically an electron impact ionizer that produces thermoelectrons from one or more incandescent filament(s) 124 and accelerates and directs the electrons causing them to collide with the gas clusters in the gas jet 118, where the jet passes through the ionizer 122. The electron impact ejects electrons from the clusters, causing a portion the clusters to become positively ionized. A set of suitably biased high voltage electrodes 126 extracts the cluster ions from the ionizer 122, forming a beam, then accelerates the cluster ions to a desired energy (typically using an acceleration potential of from about 2 keV to as much as 100 keV) and focuses them to form a GCIB 128 having an initial trajectory 154. Filament power supply 136 provides voltage $V_F$ to heat the ionizer filament 124. Anode power supply 134 provides voltage $V_A$ to accelerate thermoelectrons emitted from filament 124 to cause them to bombard the cluster containing gas jet 118 to produce ions. Extraction power supply 138 provides voltage $V_E$ to bias a high voltage electrode to extract ions from the ionizing region of ionizer 122 and to form a GCIB 128. Accelerator power supply 140 provides voltage $V_{Acc}$ to bias a high voltage electrode with respect to the ionizer 122 so as to result in a total GCIB acceleration potential equal to $V_{Acc}$ volts. One or more lens power supplies (142 and 144, for example) may be provided to bias high voltage electrodes with potentials ($V_{L1}$ and $V_{L2}$, for example) to focus the GCIB 128.

Figure 2:
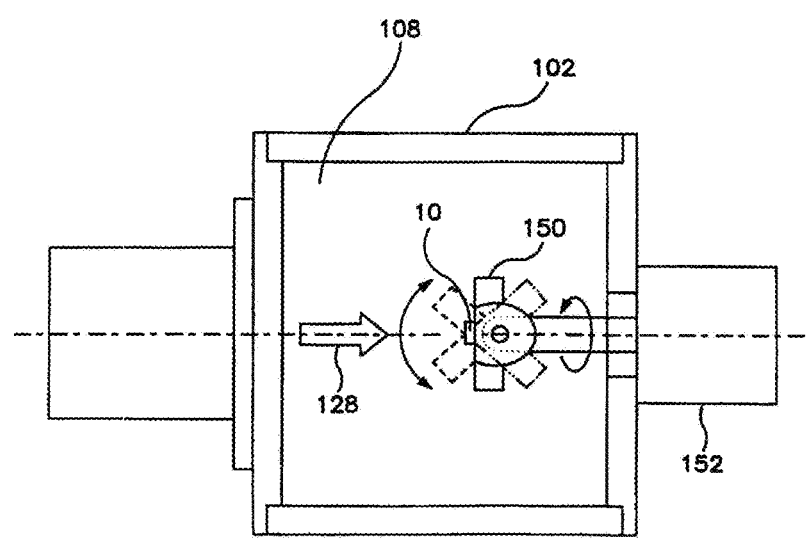
FIG. 2 is an enlarged view of a portion of the GCIB processing system, showing the workpiece holder and manipulator for handling the object to be sterilized.

Referring now to FIG. 2, a workpiece 10 to be processed by GCIB irradiation using the GCIB processor 100 is/are held on a workpiece holder 150, disposed in the path of the GCIB 128. In order to facilitate uniform processing of one or more surfaces or surface regions of the workpiece 10, the workpiece holder 150 is designed in a manner set forth below to position and/or manipulate the workpiece 10 to expose multiple surface regions for GCIB processing.

As will be explained further hereinbelow, the practice of the present invention is facilitated by an ability to control positioning of the object to be sterilized with respect to the GCIB is required to assure irradiation of all necessary surfaces of the object being sterilized. Objects being sterilized may have multiple surfaces with different surface orientations. It is desirable that there be a capability for positioning and orientating the object to be sterilized with respect to the GCIB. This requires a fixture or workpiece holder 150 with the ability to be fully articulated in order to orient all desired surfaces of a workpiece 10 to be sterilized, within the GCIB to assure incidence for the desired surface irradiation effect. More specifically, when processing a workpiece 10, the workpiece holder 150 is rotated and articulated by an articulation/rotation mechanism 152 located at the end of the GCIB processor 100.

Referring again to FIG. 1, the articulation/rotation mechanism 152 preferably permits 360 degrees of device rotation about longitudinal axis coinciding with the trajectory 154 and sufficient device articulation about an axis 157 that may be perpendicular to the longitudinal axis coinciding with the trajectory 154 to expose the objects surfaces to the GCIB for irradiation. Under certain conditions, depending upon the size of the workpiece 10, which is to be sterilized, a scanning system may be desirable to produce uniform irradiation of the medical device with the GCIB 128. Although not necessary for all GCIB processing, two pairs of orthogonally oriented electrostatic scan plates 130 and 132 may be utilized to produce a raster or other beam scanning pattern over an extended processing area. When such beam scanning is performed, a scan generator 156 provides X-axis and Y-axis scanning signal voltages to the pairs of scan plates 130 and 132 through lead pairs 158 and 160 respectively. The scanning signal voltages may be triangular waves of different frequencies that cause the GCIB 128 to be converted into a scanned GCIB 148, which scans an entire surface or extended region of the workpiece 10. As an alternative to scanning the GCIB across the workpiece 10, the workpiece holder 150 may be designed to move the medical device through a stationary GCIB in a scanning motion relative to the GCIB.

When beam scanning over an extended region is not desired, processing is generally confined to a region that is defined by the diameter of the beam. The diameter of the beam at the surface of the workpiece 10 can be set by selecting the voltages ($V_{L1}$ and/or $V_{L2}$) of one or more lens power supplies (142 and 144 shown for example) to provide the desired beam diameter at the workpiece.

Gas-cluster ion-beam processing is used in semiconductor processing and fabrication as a technology that provides extreme processing accuracy A further advantage to GCIB sterilization over other radiation techniques is the unique ability to process only the exposed surface while not having any effect on the sub-surface regions of the product. GCIB does not significantly penetrate nor permeate the object being sterilized and has no effect on the bulk portion of the object The GCIB process can be described as follows. First, the device to be sterilized is placed into a vacuum vessel mounted on suitable fixtures to allow the device to be manipulated so that all surface areas can be exposed to the GCIB beam during processing. Second, the vessel is pumped to high vacuum condition, ideally at lower than $1.3 \times 10^{-2}$ pascal pressure vacuum. Once process-level vacuum is attained in the vacuum vessel, a gate valve is opened between the processing vacuum vessel and the main GCIB tool. The gas-cluster ion-beam is then allowed to expose all surfaces of the substrate to gas-cluster ion bombardment to an exposure equal to or greater than $10^{13}$ ions per square centimeter, a level sufficient to assure cluster ion impact upon every biologically active organism. The gas clusters are typically formed from gases such as, but are not necessarily limited to argon or other noble gases, oxygen, oxygen-containing gases, other reactive gases, and mixtures of these or other gases.

Once the clusters are generated and formed into a beam, applying a high voltage accelerating potential of from 5 to 200 kV accelerates them. This high voltage potential accelerates the gas-cluster ions toward the substrate and thereby causes the clusters to impact the surface to be sterilized, releasing all their energy into that surface. The impact and energy release at the point of each cluster impact causes an intense thermal spike exceeding 1000 degrees Kelvin, but of extremely short duration, to occur only in the immediate localized region, typically in the topmost 100 angstroms only. Without wishing to be bound by a specific theory, it is believed that it may be this enormous temperature spike occurring only at the surface that destroys all biological contaminants. The high vacuum system pumps away all volatile organics and maintains a contaminant free surface state while processing continues. When the entire surface has been bombarded at the desired dose, the irradiation is terminated. The sterilized piece is now maintained in a high-vacuum contaminant-free state until the vacuum system is closed off and the vessel is returned to atmosphere by backfilling with an inert, sterile gas.

Figure 3:
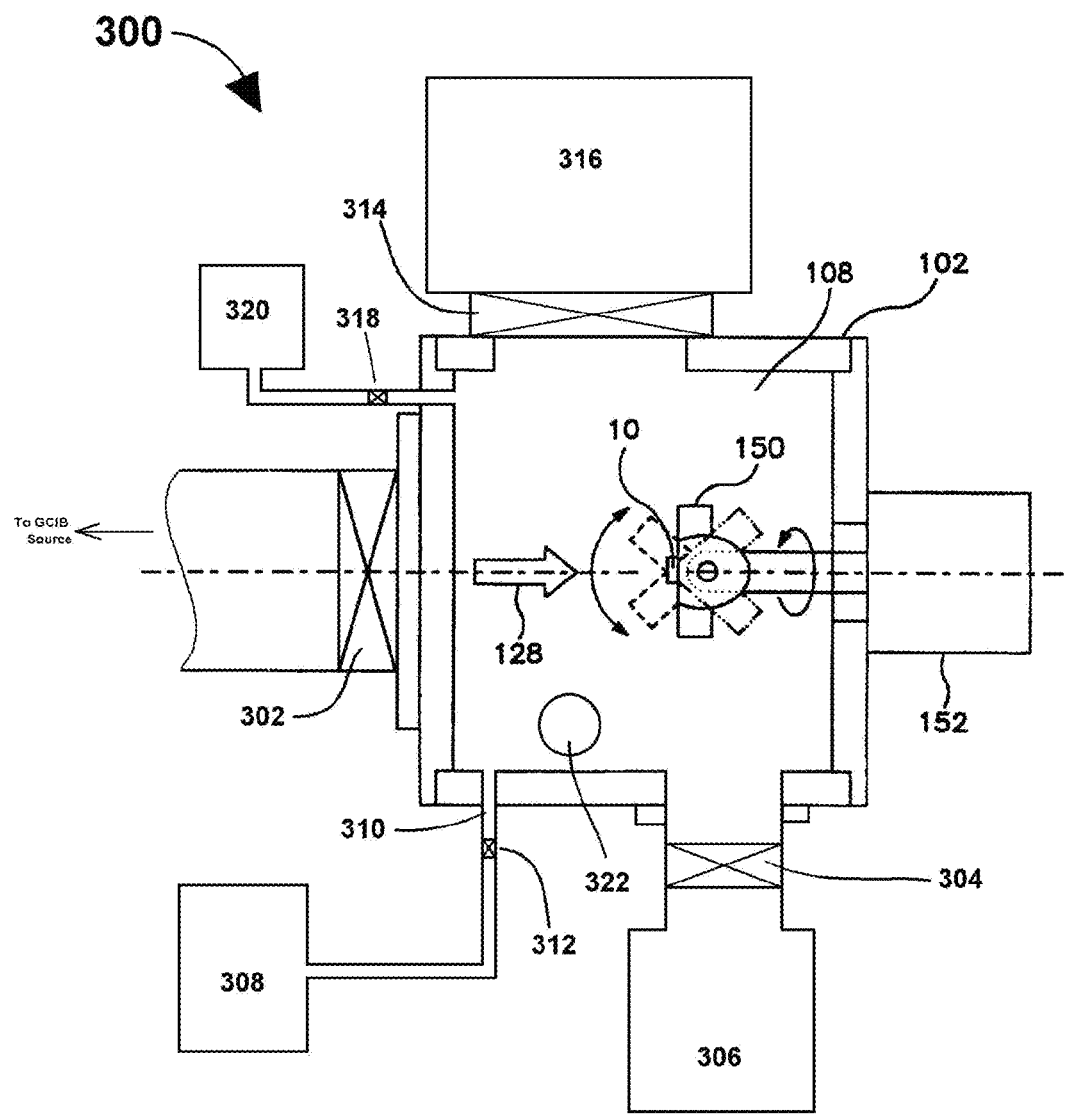
FIG. 3 is a schematic of a sterilizing system for GCIB sterilization of workpieces.

FIG. 3 is a schematic of a sterilizing system 300 specifically adapted according to the invention for GCIB sterilization processes. The vacuum vessel 102 includes a process chamber 108 that can be isolated from the GCIB source by an isolation valve 302. Isolation valve 302 has open and closed states. In the open state, isolation valve 302 permits a GCIB 128 to enter the process chamber 108 for irradiating a workpiece 10 to be sterilized while held by a workpiece holder 150. The workpiece holder 150 may be designed as previously described (during discussion of FIGS. 1 and 2 above) to rotate and/or articulate the workpiece 10 by means of articulation/rotation mechanism 152, or it may have other designs for fixedly supporting or for manipulating the workpiece 10, as will be readily apparent to those skilled in the art, for exposing single or multiple surfaces of the workpiece to the GCIB 128 (as may be required by the geometry of the workpiece and the sterilization requirements.) In the closed state, isolation valve 302 isolates the process chamber 108 from the GCIB source. The GCIB source may be similar to that shown in FIG. 1, or may be some other conventional GCIB source. The GCIB 128 provided by the GCIB source may be a scanned or an unscanned GCIB as may be suitable for the size of the workpiece 10 to be sterilized.

A vacuum system 306 is coupled to the process chamber 108 by an isolation valve 304. Isolation valve 304 has open and closed states and may be manually or automatically controlled. When in the open state, isolation valve 304 permits evacuation of the process chamber 108 by the vacuum system 306. When in the closed state, isolation valve 304 inhibits evacuation of the process chamber 108 and permits the introduction of non-vacuum atmospheres to the process chamber 108. A vent line 310 has a valve 312 for controlling introduction of a sterile venting gas 308 to the process chamber 108. A sterilant gas 320 may optionally be introduced to the process chamber 108 through valve 318 for initial sterilization of the process chamber 108 and workpiece holder 150 or for re-sterilization after a contamination event. An optional radiation source 322, which may be a short-wave ultraviolet radiation source may also be used for initial sterilization of the process chamber 108 and workpiece holder 150 or for re-sterilization after a contamination event. When an ultraviolet radiation source is used, the interior of the process chamber 108 may contain considerable reflective metal to reflect the ultraviolet radiation throughout the interior of the process chamber 108.

A loading/unloading/packaging environment 316 is coupled to the process chamber 108 by an isolation valve 314. Isolation valve 314 has an open state and a closed state. When isolation valve 314 is open, workpieces to be sterilized may be moved from the loading/unloading/packaging environment 316 to the workpiece holder 150 for GCIB sterilization. Likewise, sterilized workpieces can be moved from the workpiece holder 150 to the loading/unloading/packaging environment 316 for sterile packaging before removal from the sterilizing system 300. Conventional mechanisms and/or robotic handlers may perform the transfers and packaging of the workpiece.

In typical operation, the process chamber 108 of the sterilizing system 300 is initially cleaned and then initially sterilized. Initial sterilization of the process chamber 108, and mechanisms therein including the workpiece holder 150 may be done by evacuating process chamber 108, then closing the valves 304, 312, 302, and 314 and introducing a sterilant gas 320 to the process chamber through valve 318. After allowing adequate time for sterilization, the valve 318 may be closed and the sterilant gas evacuated from the process chamber 108 by opening isolation valve 304 and evacuating the process chamber 108 using vacuum system 306. Alternatively, the interior of the process chamber 108 and mechanisms contained therein including the workpiece holder 150 may be initially sterilized by closing valves 312, 302, 318, and 314 and evacuating the process chamber 108 through isolation valve 304 using vacuum system 306—then by activating radiation source 322, which may be a short-wave ultraviolet radiation source, to sterilize the process chamber 108 and mechanisms therein.

After initial sterilization of the process chamber 108, one or more workpiece(s) 10 to be sterilized may be loaded sequentially or in parallel onto the workpiece holder 150, evacuated, and irradiated by GCIB 128. The process chamber 108 may then be vented to atmospheric pressure using a sterile venting gas 308, and the workpiece 10 then unloaded to the loading/unloading/packaging environment 316 for packaging and/or removal from the sterilizing system 300. The loading/unloading/packaging environment 316 may enable direct insertion of sterilized work pieces into sterile containers. The load-sterilize-unload cycle may be repeated as many times as required for the sterilization job at hand.

The workpiece 10 is not exposed to sterilant gas 320 nor to radiation source 322, but rather is only sterilized by GCIB 128, avoiding exposure to toxic materials and/or undesirable effects of radiation or other sterilizing methods. The sterilization that is performed via the present invention may also be limited to certain areas to further prevent any adverse affects on the finished product from this very process.

Gas-cluster ion-beam processing may be used to perform in-situ or post-process sterilization of medical devices with specific sterilization process needs. Certain situations where other known sterilization techniques such as UV light, high temperature exposure, or wet method processing are not suitable can benefit from use of this new alternative method. Surface-only processing makes this technology attractive when compared to other methods that may cause product damage or create unwanted degradation by damaging the subsurface regions that are not a source of bio-contamination. GCIB sterilization (as a final in-situ step), in combination with other GCIB surface processing step(s), in particular GCIB-induced or GCIB-assisted drug deposition application steps, GCIB etching steps, GCIB smoothing steps, etc., make this technology particularly useful and advantageous. In such applications, the initially sterilized process chamber 108 is loaded with the workpiece 10, multiple GCIB processing steps including a GCIB sterilizing step are preformed, and the finished product removed and optionally packaged.

Specific applications of the present invention include drug eluting implants and implants having areas adapted for enhanced cell growth. Drug eluting implants, such as stents, which finely control the area of coated drugs can be created using the present invention. Implants with areas adapted for enhanced cell growth using GCIB can be sterilized as part of the GCIB process to further reduce any risk of contamination.

The advantages of using GCIB processing are numerous and can be generalized as follows: First, the processing is carried out in a vacuum environment which provides complete environmental control over biological contamination and provides safe storage until the packaging process can begin. Second, the GCIB process affects only a shallow surface layer, leaving the underlying material undamaged and creating no sub-surface damage or degradation. Third, GCIB allows extreme heat sterilization of the immediate surface without significantly heating the bulk material, thus allowing sterilization of temperature-sensitive materials at approximately ordinary room temperatures. Another benefit of GCIB sterilization is the avoidance of ultraviolet, x-ray, or gamma ray, or other types of damage caused by other conventional techniques that can cause degradation of many materials. The combination or individual merits of these advantages may make GCIB sterilization attractive for situations that cannot tolerate wet processing, ultraviolet exposure or oxidative environments or situations where environmental control is difficult prior to packaging.

While GCIB has advantages in many applications, there are also limitations that must be considered before choosing GCIB sterilization processing. First, the product for sterilization must be vacuum compatible. This means that the product must be able to withstand the rigors of the vacuum process without damage, and that the product is compatible with a vacuum level suitable for GCIB processing. Further, it is important that this vacuum level can be maintained while processing without excessive product out-gassing that may adversely affect the GCIB process. Lastly, GCIB is a "line of sight" process, which means that all surfaces of the sample that are intended to be sterilized must be exposed to the beam for the process to work. Depending on the shape and complexity of the object being sterilized, this may require very elaborate fixtures and manipulation tools and may prove to be impractical or impossible for some complex shapes. For many shapes and geometries, the required multiple exposures can be readily accomplished by manipulating, rotating, articulating, and/or repositioning the object during processing using conventional holding mechanisms that will be readily known by those skilled in the art.

Exemplary Embodiment

Titanium was selected as an exemplary substrate for evaluation of GCIB sterilization since titanium is one of several commonly employed materials for implantable medical devices and prostheses. Titanium foil was cut into pieces of approximately 1.5 cm×1.5 cm square. The cut pieces of titanium foil were openly exposed to ambient atmosphere in an inhabited area for 24 hours to promote the incidence of bacteria and/or bacterial spores to attach to the surface of the titanium foil squares. Following ambient exposure, Group 1 of the titanium foil squares was treated with argon GCIB irradiation at 30 kV acceleration potential with $5 \times 10^{14}$ ions/$cm^2$ dose on both sides, for a total GCIB irradiation time of 90 seconds. Following ambient exposure, Group 2 was sterilized using a conventional sterilization process by being placed in a sterilization pouch and subjected to 20 minutes in a Harvey® Chemiclave 5000 sterilizer with Harvey® Vapo-Sterile solution. As a control, Group 3 was not further treated after the exposure to ambient atmosphere. Foil from each group was placed in individual pre-warmed LB-Agar (Luria Bertani Agar, a general purpose, non preferential, bacterial culture medium) plates (Sigma L5542) and placed in a 37° C. incubator for 72 hours and bacterial colonies were visually quantified.

Figure 4A:
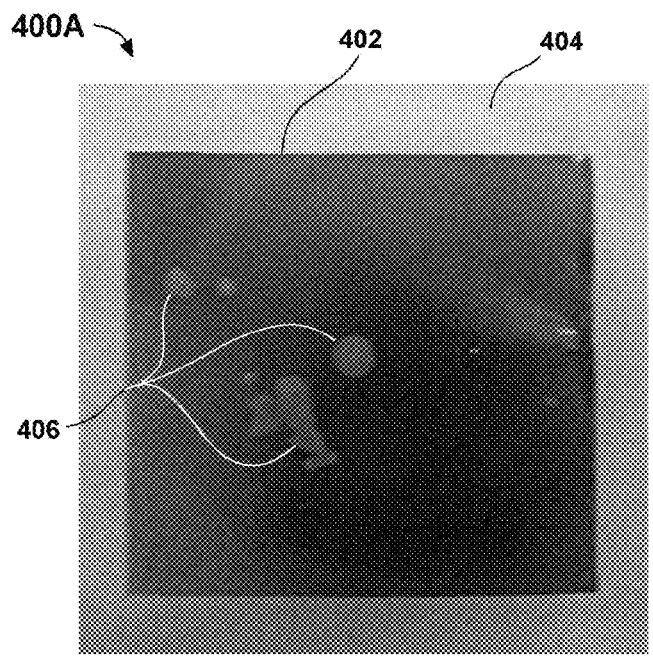
FIG. 4A is a photograph of a control titanium foil showing bacterial colonies growing thereon.

FIG. 4A shows a photograph 400A of a Group 3 (control group) titanium foil piece 402 in agar medium 404 showing the presence of numerous bacterial colonies growing on the foil several exemplary bacterial colonies 406 are indicated on the photograph.

Figure 4B:
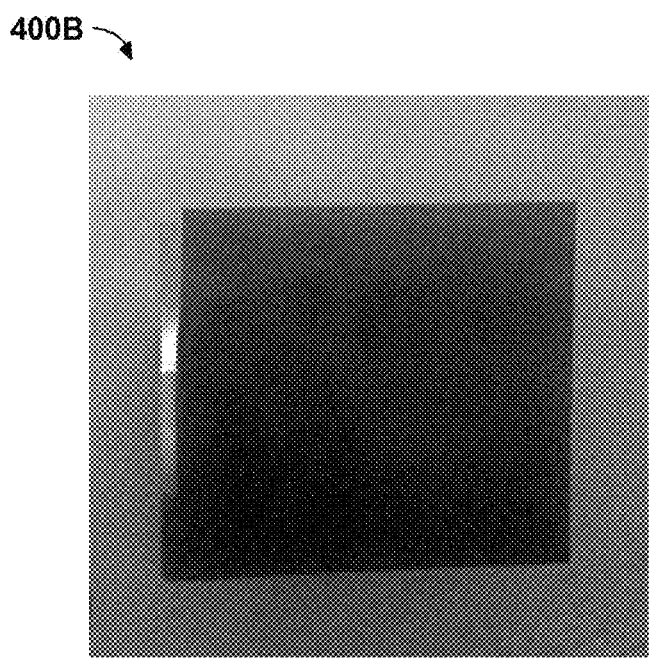
FIG. 4B is a photograph of a conventionally sterilized titanium foil showing no bacterial colonies growing thereon.

FIG. 4B shows a photograph 400B of a Group 2 (conventionally sterilized) titanium foil piece in agar medium showing complete absence of bacterial colonies, indicating sterilization after ambient exposure.

Figure 4C:
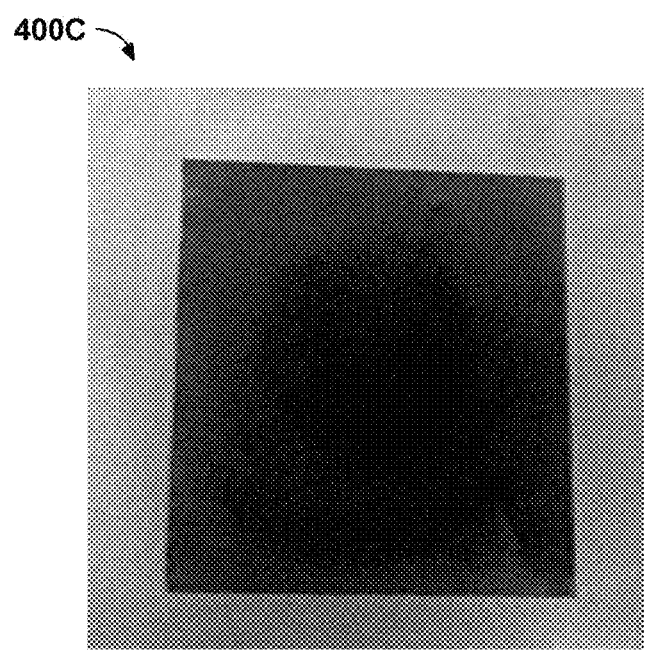
FIG. 4C is a photograph of a GCIB irradiated titanium foil showing no bacterial colonies growing thereon, indicating effectiveness of GCIB sterilization.

FIG. 4C shows a photograph 400C of a Group 1 (GCIB sterilized) titanium foil piece in agar medium, again showing complete absence of bacterial colonies, indicating the effectiveness of the GCIB sterilization after ambient exposure.

Both Groups 1 and 2 had no bacterial colonies present, representing 0% surface area occupied by colonies. In comparison, the untreated control Group 3 had 27 visible bacterial colonies, several of which may have been the product of multiple colonies merging into a larger colony. All of the control Group 3 samples had visible bacterial colonies. None of the Group 1 or Group 2 samples had visible bacterial colonies. The total titanium surface covered by bacterial colonies for the control Group 3 was about 15%.

Although the invention has been described with respect to various embodiments, it should be realized this invention is also capable of a wide variety of further and other embodiments within the spirit and scope of the invention and the appended claims.

It is claimed:

1. A method for sterilizing a workpiece comprising the steps of:
   providing a chamber having an interior and a workpiece holder;
   initially sterilizing the workpiece holder and the interior of the chamber;
   loading a workpiece onto the workpiece holder to be held thereby;
   forming a first accelerated gas-cluster ion-beam;
   directing the first accelerated gas-cluster ion-beam onto the workpiece;
   first processing the workpiece by irradiating at least a first portion of the surface of the workpiece with the first accelerated gas-cluster ion-beam;
   discontinuing first processing when the at least a first portion of the surface of the workpiece has received a predetermined dose;
   forming a second accelerated gas-cluster ion-beam;
   directing the second accelerated gas-cluster ion-beam onto the workpiece;
   second processing the workpiece by irradiating at least a second portion of the surface of the workpiece with the second accelerated gas-cluster ion-beam;
   discontinuing second processing when the at least a second portion of the surface of the workpiece has received a predetermined dose;
   unloading the workpiece from the workpiece holder and removing it from the chamber; and
   wherein either of the first processing step or the second processing step is a sterilizing step.

2. The method of claim 1 wherein the at least a first portion of the surface and the at least a second portion of the surface are the same portion of the surface.

3. The method of claim 1, further comprising rotating, articulating, repositioning, or moving the workpiece during the steps of first processing or second processing to provide for receiving an irradiated gas-cluster ion-beam dose on multiple portions of the surface of the workpiece.

4. The method of claim 1, further comprising unloading the workpiece directly into a sterile container.

5. The method of claim 1, wherein at least one of the steps of first processing or second processing introduces a dose of at least $10^{13}$ ions/$cm^2$ to an irradiated portion of the surface of the workpiece.

6. The method of claim 1, wherein the forming step of the first or second accelerated gas-cluster ion beam includes accelerating the respective gas-cluster ion-beam using an acceleration potential of at least 2 kV.

7. The method of claim 1, wherein the forming step of the first or second accelerated gas-cluster ion-beam comprises forming a gas-cluster ion-beam comprising a noble gas or a mixture of a noble gas with oxygen.

8. The method of claim 1, wherein the first or second portion of a surface is an entire surface.

* * * * *